United States Patent
Dusci et al.

(10) Patent No.: US 10,888,534 B2
(45) Date of Patent: Jan. 12, 2021

(54) STORAGE STABLE READY-TO-USE NOREPINEPHRINE AQUEOUS SOLUTIONS IN FLEXIBLE PLASTIC BAGS

(71) Applicant: InfoRLife SA, Campascio (CH)

(72) Inventors: Sergio Dusci, Tresivio (IT); Sayan Dusci, Tresivio (IT)

(73) Assignee: InfoRLife SA, Campascio (CH)

( * ) Notice: Subject to any disclaimer, the term of this patent is extended or adjusted under 35 U.S.C. 154(b) by 0 days.

(21) Appl. No.: 16/395,541

(22) Filed: Apr. 26, 2019

(65) Prior Publication Data

US 2020/0338020 A1    Oct. 29, 2020

(51) Int. Cl.
*A61K 31/137*  (2006.01)
*A61K 47/02*   (2006.01)
*A61J 1/10*    (2006.01)

(52) U.S. Cl.
CPC .............. *A61K 31/137* (2013.01); *A61J 1/10* (2013.01); *A61K 47/02* (2013.01)

(58) Field of Classification Search
CPC .......... A61K 31/137; A61K 47/02; A61J 1/10
See application file for complete search history.

(56) References Cited

U.S. PATENT DOCUMENTS

| | | | | |
|---|---|---|---|---|
| 6,007,529 A | * | 12/1999 | Gustafsson | A61J 1/00 604/410 |
| 2007/0029001 A1 | | 2/2007 | Trouilly et al. | |
| 2007/0031976 A1 | | 2/2007 | Trouilly et al. | |
| 2007/0092579 A1 | | 4/2007 | Trouilly et al. | |
| 2017/0049720 A1 | * | 2/2017 | Mitidieri | A61K 9/0019 |
| 2018/0214394 A1 | | 8/2018 | Puri et al. | |
| 2018/0243243 A1 | | 8/2018 | Yadav et al. | |
| 2019/0046473 A1 | | 2/2019 | Hingorani et al. | |
| 2019/0046474 A1 | | 2/2019 | Hingorani et al. | |
| 2019/0133972 A1 | | 5/2019 | Hingorani et al. | |
| 2019/0133973 A1 | | 5/2019 | Hingorani et al. | |

FOREIGN PATENT DOCUMENTS

WO    WO 2007/016615 A1    2/2007
WO    WO 2015/128418 A1    9/2015

OTHER PUBLICATIONS

Levophed, Jun. 2007, Hospira, 5 pages. (Year: 2007).*
International Search Report and Written Opinion dated Feb. 12, 2020, in PCT/IB2019/001079, 13 pages.

* cited by examiner

*Primary Examiner* — Trevor Love
(74) *Attorney, Agent, or Firm* — Oblon, McClelland, Maier & Neustadt, L.L.P.

(57) ABSTRACT

A sterile, sulfite-free aqueous norepinephrine solution comprising up to about 0.2 mg/ml of norepinephrine concentration (as free base), a tonicity adjusting agent, at a pH where the norepinephrine is soluble which is packaged in a flexible plastic container, characterized by being storage stable for from about 12 months to about 24 months at room temperature of about 25° C.

15 Claims, 1 Drawing Sheet

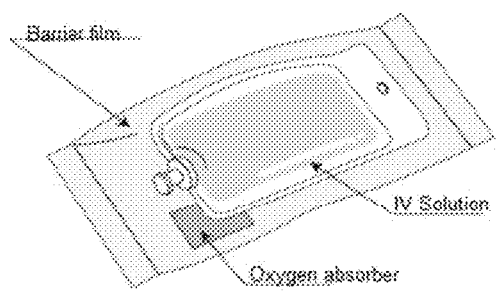

STORAGE STABLE READY-TO-USE NOREPINEPHRINE AQUEOUS SOLUTIONS IN FLEXIBLE PLASTIC BAGS

FIELD OF THE INVENTION

This invention relates to ready-to-use norepinephrine intravenous solutions (IV) in flexible plastic bags which are storage stable at room temperature for 12 to 24 months. In particular, the invention relates to storage stable norepinephrine IV solutions which do not contain an antioxidant.

BACKGROUND OF THE INVENTION

Norepinephrine is currently available as concentrated solutions of norepinephrine, 1 mg/ml, containing an antioxidant, typically sodium metabisulfite, in an amount of 2 mg/ml, to improve stability. The concentrated solutions are sold in glass vials. Prior to use the concentrated solution must be diluted in an IV solution, most often in 5 wt. % dextrose, sodium chloride solution 0.9%, or a mixed 5 wt. % dextrose and sodium chloride solution. The package label advises disposing of the diluted IV solution within 24 hours of preparation.

The concentrated norepinephrine solutions are typically diluted to a concentration of between about 0.016 mg/ml to 0.064 mg/ml. The step of diluting the concentrated solutions introduces the possibility of microbial contamination and the possibility of dilution errors. The presence of antioxidants, in particular sulfites and bisulfites, introduces a health risk which should be avoided if possible.

The dilution of concentrated norepinephrine solutions is not recommended because the dextrose solution provides for greater pH control. The solution pH is important since the norepinephrine degradation is pH dependent. The use of dextrose solutions is often not desired because of the risk of hyperglycemia which can be detrimental. Norepinephrine is used to restore the blood pressure of hypotensive patients to the normal range. Norepinephrine is also used during cardiac resuscitation to restore and maintain an adequate blood pressure after effective heartbeat and ventilation have been restored.

Since the drug is used with seriously compromised patients, a need exists for an IV solution which is free of antioxidants.

A still further need exists for norepinephrine IV solution which is substantially free of dextrose to avoid the possible complication of hyperglycemia.

A still further need exists for a ready-to-use norepinephrine IV solution to avoid compounding errors.

Yet another need is for norepinephrine IV solutions which can be stored at room temperature for 12 to 24 months to allow a medical facility to keep the IV solution in the intensive care units and emergency rooms without the need for handling the concentrated solution.

BRIEF SUMMARY OF THE INVENTION

The invention involves storage stable, ready-to-use norepinephrine IV solutions substantially free of dextrose and antioxidant, packaged in a flexible plastic container which has a storage life at ambient temperature (25° C.) of from 12 to 24 months or more. The IV solution contains, in addition to water, a tonicity adjusting agent such as sodium chloride or calcium chloride or a mixture thereof. Other tonicity adjusting agents may be used. For the best shelf life sugars are not used. However, sugars may be used if a reduced shelf-life is acceptable.

BRIEF DESCRIPTION OF THE DRAWINGS

Drawing FIG. 1 illustrates one embodiment of the invention showing the IV bag, the associated pouch and oxygen absorber.

DETAILED DESCRIPTION OF THE INVENTION

Norepinephrine is available as the bitartrate salt:

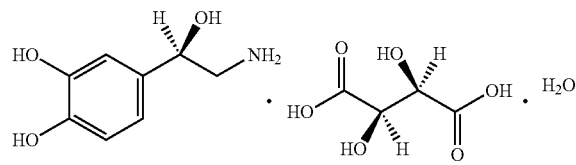

The salt form of norepinephrine is used because it is more soluble than the free base. While the tartrate salt is preferred, any pharmaceutically acceptable salt having the necessary solubility may be used. In this specification the norepinephrine concentration is reported as that of the free base.

Studies have shown that norepinephrine IV saline solutions when stored at room temperature after 61 days have less than 90% (87%) of the norepinephrine remaining. Walker et al., Can, J. Hosp. Pharm; 63(2):113-118 at 117. This falls below the 90% minimum set by the FDA for determining shelf life and falls well short of the one to two years or more of shelf life needed for a commercial product. The same product when stored at 4° C. had 95.6% remaining after 61 days. However, even storage at 4° C. would not meet the one year requirement as by about the $5^{th}$ month the amount of norepinephrine remaining would be expected to have fallen below 90%. The norepinephrine concentrated solution, although not disclosed, would have contained sodium metabisulfite.

The present ready-to-use solutions comprise a pharmaceutically acceptable norepinephrine salt, preferably the bitartrate, water and a sufficient quantity of a non-sugar tonicity adjusting in an amount to provide an osmolality of between about 250 and about 350 mosm/kg; preferably enough to make the solution isotonic, and more preferably an osmolality of between about 260 and about 320 mosm/kg. When sodium chloride is used as the tonicity adjusting agent, the amount of sodium chloride added is sufficient to provide the desired osmolality, preferably between about 8 and 10 mg/ml, preferably between about 8.5 and 9.5 mg/ml, and most preferably about 9 mg/ml. Other tonicity adjusting agents may be used. If desired, a pharmaceutical commercial saline IV solution can be used. The amount of water used is an amount sufficient to bring the solution to the desired concentration.

The IV solution preferably has a norepinephrine concentration (as free base) between about 0.010 and 0.2 mg/ml more preferably between 0.015 and 0.07 mg/ml, with the most preferred concentrations being 0.016, 0.032 and 0.064 mg/ml of norepinephrine. Other concentrations may also be used if desired.

The pH of the aqueous solution is between about 2.5 and 5.0, more preferably between about 2.75 and 4.5 and most preferably between about 3.4 and 3.8. The pH may be adjusted with a pharmaceutically acceptable acid; mineral acids are preferred, most preferably hydrochloric acid. A base may be used to adjust the pH to the desired range. Any pharmaceutically acceptable base may be used; sodium hydroxide is preferred.

The mixture is filled into bags. The filling need not be aseptic if the bags are to be terminally sterilized. However, to obtain the maximum shelf life of two years or more, aseptic filling is necessary. When terminal sterilization is used the shelf life is about one year.

The flexible plastic IV bag is then overwrapped with a secondary packaging to form an outer bag. The material for the overwrapping is not critical so long as it has a low oxygen permeability. The preferred overwrapping is an aluminum pouch in which the IV bag is placed and the pouch sealed with or without a transparent window to allow to see the oxygen indicator without opening the overwrapping. Because norepinephrine is sensitive to oxygen prior to sealing the outer pouch an oxygen absorber and an indicator is placed in the bag. Oxygen indicators are well-known and are available from DryPak Industries and Sorbent Systems and others. The oxygen indicator changes color as the oxygen content in the overwrap pouch changes. In many systems the indicator has a pink color when the oxygen is low changing to blue or purple as the oxygen level increases.

It is also preferred to include a conventional oxygen absorber such as those in food packaging. One such absorber is sold by Mitsubishi Gas Chemical under the trade name AGELESS® SS-MBC, and others include the Standa ATCO oxygen absorbers. Oxygen absorbers whose use has been previously approved by the FDA are preferred, to simplify the FDA regulatory review process. The amount of oxygen absorber present is not critical so long the amount is sufficient to remove any oxygen in the pouch and bag, and it may range from 1 to 4 or 5 packets of material. The amount to be used is determined by the amount of oxygen in the bag and pouch after sealing. This can be readily determined by routine experimentation either by directly measuring the amount of oxygen or by preparing test bags and pouches with differing amounts of oxygen absorber and selecting the amount which results in an oxygen level low enough for the desired shelf life; preferably enough oxygen absorber is used so the pouch and bag are essentially oxygen free. This is determined by allowing the bag and pouch assembly to equilibrate with the oxygen absorber and then checking the absorber's color to determine if it still has the ability to absorb oxygen. This is an indication of an essentially oxygen-free environment. A single packet is usually enough. The oxygen absorber is an iron powder which absorbs oxygen in the space between the overwrap and the IV pouch and in the IV bag. The arrangement is shown in drawing FIG. 1.

The use of the overwrap pouch, the oxygen indicator and the oxygen absorber in the pouch eliminates the need for an antioxidant in the IV solution. Thus, the use of these is preferred but is not necessary. The oxygen indicator warns the user that the pouch's integrity may have been breached and that the norepinephrine may have degraded and is out of specification.

The flexible plastic container must be one which is compatible with norepinephrine. If the package is to be terminally sterilized, it must also be able to undergo heat sterilization in moist steam without contaminating the norepinephrine solution. Suitable flexible plastic containers are those made of copolymerized ethylene and vinyl acetate. Preferably the bag is laminated with the inner most layer comprising copolymerized ethylene and vinyl acetate. More preferably the bag comprises from 3 to 7 layers. These materials are commercially available under the tradename Nexcel® by Sealed Air. The volume of the bag is dependent on the volume of premixed formula. The volume of premixed formula can be from 10 ml to 1000 ml, preferably 50 ml and 100 ml based on current norepinephrine dosing. Larger or smaller volumes can be used depending on dosing requirements. CR3 elastomer copolyester ether bags may also be used for formulations to be sterilized in moist steam, but are not preferred.

In an embodiment of the present invention, provided are a flexible plastic container with modified ports and closure system suitable for storing norepinephrine formulations of the present invention which is typically subjected to product sterilization by steam sterilization (e.g., autoclaving, 121° C. for about 20 minutes) without altering the thermal properties of the film layers, ports and closure system as well as maintaining the integrity of the container. The primary polymeric materials which may be used include: polysulfone, polycarbonate, polypropylene, polyethylene (LDPE or HDPE), ethylene/propylene copolymers, polyolefins, acrylic-imide copolymers, polyester (e.g. PET, PEN and the like), Teflon, Nylon, acetal (Delrin), polymethylpentene, PVDC, ethylvinylacetate, AN-copolymer etc. In addition to plastic bags, CZ resin containers, polypropylene and similar resins can be used as rigid containers and syringes.

The ports and the closure system preferably use commerciality available polymers, elastomers etc. In an exemplary embodiment of the present invention, the administrative and additive ports can be made of external coextruded layer consisting of synthetic thermoplastic rubber (Raumedic SRT320) ranging from about 20 to 30% based on an elastomer modified polypropylene. In some embodiments, the internal coextruded layer (PE770) of not more than 50% in composition consists of ethylene vinyl acetate without any further additives (EVA). The tubing ports can be made of two-layer materials, which can withstand both terminal sterilization and beta ray sterilization. Furthermore, the twist-off compositions can be made of polyproplene Granuflex® 4489 between 70-80% and Granuflex®4371 15-20%. Alternatively the port tube may be a bilayer tube comprising an outer layer of polypropylene and an inner layer of EVA and the twist off made of LDPE and PP. However, other polymers that are stable, that have low leachables, and that resist physical deformation may also be used for the ports and closure assemblies.

Commercially available flexible plastic containers (bags) such as Excel® (Braun Company) comprising a three-layered ethylene-polypropylene bag having polyester elastomer outer layer, Visiv® (Hospira), Nexcel® (Sealed Air), Intervia® (Baxter) preferably with a non-DEHP fluid path, Technoflex polyolefin bags, etc., for pharmaceutical formulation or medical liquids are assembled of different plastic materials of different properties, thermal resistance and functionalities. They are typically designed and tested mostly for aqueous formulations admixtures, premixed or ready-to-use pharmaceutical products. Still the combination of the water and drug composition subjected to further Beta ray sterilization can adversely affect plastic materials, sealing integrity unless they are maintained at certain conditions. Thus, the plastic container should be checked after sterilization for integrity before using it for the formulation. In addition, the formulation after sterilization should be analyzed for the presence of substances leached from the container as a result of the filling cycle.

In another alternative embodiment, provided are a flexible plastic container with modified ports and closure system suitable for storing norepinephrine formulations of the present invention which is typically subjected to product sterilization by steam sterilization (e.g., autoclaving, 121° C. for about 15 to 20 minutes) without altering the thermal properties of the film layers, ports and closure system as well as maintaining the integrity of the container. The primary polymeric materials which may be used include: polysulfone, polycarbonate, polypropylene, polyethylene (LDPE or HDPE), ethylene/propylene copolymers, polyolefins, acrylic-imide copolymers, polyester (e.g. PET, PEN and the like), Teflon, Nylon, acetal (Delrin), polymethylpentene, PVDC, ethylvinylacetate, AN-copolymer etc.

Preferably the norepinephrine IV solution is packaged aseptically using conventional aseptic packaging conditions as described in the FDA Guidance for Industry: Sterile Drug Products Produced by Aseptic Processing—Current Good Manufacturing Practice, 2004, the content of which is incorporated by reference herein in its entirety. A preferred sequence of steps in the aseptic filling process involves first dissolving the norepinephrine bitartrate and sodium chloride, the tonicity adjusting agent, in water. The solution is then pre-filtered thru a 0.45 μm rated filter followed by two filtrations using 0.2 μm filters followed by filling the flexible plastic bag and sealing in aseptic conditions under Laminar Flow. The external surfaces of the flexible plastic bag are decontaminated and the bag then enclosed by the overwrap pouch which is sealed. Preferably the overwrap pouch contains an oxygen indicator and an oxygen absorber.

In certain embodiments, dissolved oxygen in the norepinephrine solution may be removed prior to filling the flexible plastic container with the solution. This removal of dissolved oxygen may be performed by deaerating or degassing the solution by bubbling or blowing an inert gas. This removal of dissolved oxygen also may be performed by deaerating or degassing water by bubbling or blowing an inert gas, prior to dissolving the norepinephrine in the water.

In other, preferred, embodiments, dissolved oxygen in the norepinephrine solution is not removed prior to filling the flexible plastic container with the solution. In such embodiments, dissolved oxygen either is (i) not removed from the water prior to dissolving the norepinephrine in the water, (ii) not removed from the solution after dissolving the norepinephrine in the water, or both (i) and (ii). For example, such embodiments do not include performing deaerating or degassing by bubbling or blowing an inert gas, either (i) on the water prior to dissolving the norepinephrine in the water, (ii) on the solution after dissolving the norepinephrine in the water, or both (i) and (ii). Not removing dissolved oxygen from the solution before filling the flexible plastic container with the solution advantageously simplifies the process of preparing the solution.

In embodiments in which dissolved oxygen in the norepinephrine solution is not removed prior to filling the flexible plastic container with the solution, the filling of the flexible plastic container with the norepinephrine solution may be performed in an air environment, rather than in an inert gas environment. That is, oxygen can be present in the environment when filling the flexible plastic container with the norepinephrine solution; an oxygen-free inert gas environment is not required.

Aseptically sterilized norepinephrine solutions are preferred because of their longer storage stability at room temperature (20° C.), over 24 months for all concentrations, 0.016, 0.032 and 0.064 mg/ml. Terminally sterilized norepinephrine solutions at concentrations of 0.032 mg/ml and 0.016 mg/ml are also storage stable at room temperature for 24 months, while norepinephrine concentrations of 0.064 mg/ml are stable at room temperature for between about 12 and 20-24 months. At 24 months the solution has a brown color and contains only about 88% of the initial norepinephrine concentration. Thus, in certain embodiments, "storage stable" in the present application means that the norepinephrine solution (i) remains clear and colorless, (ii) contains 90% or more of an initial amount of norepinephrine, or both (i) and (ii), after a specified period of storage time.

EXAMPLES

The following examples were prepared as follows:

|  | Reference Table 1<br>64 μg/mL<br>(with antioxidant)<br>Terminally sterilized | Reference Table 2<br>64 μg/mL (without antioxidant)<br>Terminally sterilized |
|---|---|---|
| Norepinephrine Base (as Norepinephrine Bitartrate Monohydrate) | 0.064 mg<br>0.128 mg | 0.064 mg<br>0.128 mg |
| Dextrose Monohydrate | 50 mg | 50 mg |
| Sodium Metabisulfite | 0.128 mg | N.A. |
| NaOH or HCl 37% (diluted) | q.s. to pH 3.4-3.6 | |
| WFI (not deaerated) | q.s. to 1 mL | |

|  | Reference Table 3<br>16 μg/mL<br>(with antioxidant)<br>Terminally sterilized | Reference Table 4<br>16 μg/mL (without antioxidant)<br>Terminally sterilized |
|---|---|---|
| Norepinephrine Base (as Norepinephrine Bitartrate Monohydrate) | 0.016 mg<br>0.032 mg | 0.016 mg<br>0.032 mg |
| Sodium Chloride | 9 mg | 9 mg |
| Sodium Metabisulfite | 0.032 mg | N.A. |
| NaOH or HCl 37% (diluted) | q.s. to pH 3.4-3.6 | |
| WFI (not deaerated) | q.s. to 1 mL | |

| Ingredients | Reference Table 6<br>16 μg/mL<br>(terminally sterilized vs not sterilized) | Reference Table 5<br>64 μg/mL<br>(terminally sterilized vs not sterilized) |
|---|---|---|
| Norepinephrine Base (as Norepinephrine Bitartrate Monohydrate) | 0.016 mg<br>0.032 mg | 0.064 mg<br>0.128 mg |
| Sodium Chloride | 9 mg | 9 mg |
| NaOH or HCl 37% (diluted) | q.s. to pH 3.4-3.6 | |
| WFI (not deaerated) | q.s. to 1 mL | |

| Ingredients | Reference Table 7<br>16 μg/mL<br>(with oxygen absorber) NOT terminally sterilized | Reference Table 8<br>64 μg/mL<br>(with oxygen absorber) NOT terminally sterilized |
|---|---|---|
| Norepinephrine Base (as Norepinephrine Bitartrate Monohydrate) | 0.016 mg<br>0.032 mg | 0.064 mg<br>0.128 mg |
| Sodium Chloride | 9 mg | 9 mg |
| NaOH or HCl 37% (diluted) | q.s. to pH 3.4-3.6 | |
| WFI (not deaerated) | q.s. to 1 mL | |

The above solutions were subjected to stability testing as shown in the following tables. The temperature in the tests of Tables 1-4 was 25° C.

TABLE 1

(Norepinephrine Inj. 64 μg/mL in 5% dextrose with antioxidant)

| TEST | UNIT | LIMITS | T = 0 Not Ster. | T = 0 | T = 2M | T = 3M | T = 6M | T = 9M | T = 12M |
|---|---|---|---|---|---|---|---|---|---|
| Color and Clarity | — | No pinkish solution/No precipitate | Complies | Complies | Complies | Complies | Complies | Complies | Complies |
| pH | pH unit | 3.0-4.5 | 3.5 | 3.5 | 3.5 | 3.5 | 3.5 | 3.5 | 3.5 |
| Osmolality | mOsmol/Kg | 270-320 | 272 | 273 | 272 | 271 | 272 | 277 | 271 |
| ASSAY | % | 90.0-115.0 | 100 | 94.8 | 94.7 | 94.4 | 94.1 | 92.7 | 93.1 |

TABLE 2

(Norepinephrine Inj. 64 μg/mL in 5% dextrose without antioxidant)

| TEST | UNIT | LIMITS | T = 0 Not Ster | T = 0 | T = 2M | T = 3M | T = 6M | T = 9M | T = 12M |
|---|---|---|---|---|---|---|---|---|---|
| Color and Clarity | — | No pinkish solution/No precipitate | Complies | Complies | Slightly brown | Slightly brown | Slightly brown | Slightly brown | Slightly brown |
| pH | pH unit | 3.0-4.5 | 3.5 | 3.5 | 3.5 | 3.5 | 3.5 | 3.5 | 3.5 |
| Osmolality | mOsmol/Kg | 270-320 | 271 | 270 | 270 | 272 | 270 | 272 | 268 |
| ASSAY | % | 90.0-115.0 | 100 | 97.8 | 97.0 | 96.9 | 96.3 | 95.5 | 96.0 |

TABLE 4

(Norepinephrine Inj. 16 μg/mL in 0.9% NaCl without antioxidant)

| TEST | UNIT | LIMITS | T = 0 Not Ster. | T = 0 | T = 2M | T = 3M | T = 6M | T = 9M | T = 12M |
|---|---|---|---|---|---|---|---|---|---|
| Color and Clarity | — | No pinkish solution/No precipitate | Complies | Complies | Complies | Complies | Complies | Complies | Complies |
| pH | pH unit | 3.0-4.5 | 3.6 | 3.6 | 3.6 | 3.6 | 3.5 | 3.6 | 3.6 |
| Osmolality | mOsmol/Kg | 270-320 | 289 | 288 | 288 | 288 | 288 | 288 | 288 |
| ASSAY | % | 90.0-115.0 | 101.2 | 100.7 | 97.6 | 97.5 | 97.1 | 94.8 | 92.6 |

TABLE 3

(Norepinephrine Inj. 16 μg/mL in 0.9% NaCl with antioxidant)

| TEST | UNIT | LIMITS | T = 0 Not Ster. | T = 0 | T = 2M | T = 3M | T = 6M | T = 9M | T = 12M |
|---|---|---|---|---|---|---|---|---|---|
| Color and Clarity | — | No pinkish solution/No precipitate | Complies | Complies | Complies | Complies | Complies | Complies | Complies |
| pH | pH unit | 3.0-4.5 | 3.6 | 3.6 | 3.6 | 3.6 | 3.6 | 3.6 | 3.6 |
| Osmolality | mOsmol/Kg | 270-320 | 290 | 290 | 286 | 286 | 296 | 288 | 285 |
| ASSAY | % | 90.0-115.0 | 101.7 | 100.4 | 98.5 | 99.1 | 99.1 | 97.3 | 95.1 |

TABLE 5

Norepinephrine 64 μg/mL in 0.9% NaCl Sterilized vs not sterilized (40° C.)

Norepinephrine — Storage condition: 40° C. ± 2° C./RH 15% ± 5%

| Inj. 64 μg/mL in 0.9% NaCl TEST | PROPOSED LIMIT | T = 0 Ster. | T = 1M 40° C. (Ster.) | T = 2M 40° C. (Ster.) | T = 3M 40° C. (Ster.) | T = 6M 40° C. (Ster.) | Δ | UNIT |
|---|---|---|---|---|---|---|---|---|
| *Sterilized* | | | | | | | | |
| Appearance of Solution | Clear and colourless | Clear and colourless | Clear and colourless | Clear and colourless | Clear and colourless | Brown solution | — | — |
| Assay | 90.0-115.0 | 98.7 | 98.6 | 96.9 | 93.4 | 88.2 | −10.5 | % |
| *Not Sterilized* | | | | | | | | |
| Appearance of Solution | Clear and colourless | Clear and colourless | Clear and colourless | Clear and colourless | Clear and colourless | Clear and colourless | — | — |
| Assay | 90.0-115.0 | 99.8 | 97.5 | 96.1 | 100.3 | 99.2 | −0.6 | % |

TABLE 6

Norepinephrine 16 μg/mL in 0.9% NaCl Sterilized vs not sterilized (40° C.)

Norepinephrine — Storage condition: 40° C. ± 2° C./RH 15% ± 5%

| Inj. 16 μg/mL in 0.9% NaCl TEST | PROPOSED LIMIT | T = 0 Ster. | T = 1M 40° C. (Ster.) | T = 2M 40° C. (Ster.) | T = 3M 40° C. (Ster.) | T = 6M 40° C. (Ster.) | Δ | UNIT |
|---|---|---|---|---|---|---|---|---|
| *Sterilized* | | | | | | | | |
| Appearance of Solution | Clear and colourless | Clear and colourless | Clear and colourless | Clear and colourless | Clear and colourless | Clear and colourless | — | — |
| Assay | 90.0-115.0 | 99.7 | 98.6 | 99.6 | 99.5 | 98.9 | −0.8 | % |
| *Not Sterilized* | | | | | | | | |
| Appearance of Solution | Clear and colourless | Clear and colourless | Clear and colourless | Clear and colourless | Clear and colourless | Clear and colourless | — | — |
| Assay | 90.0-115.0 | 100.6 | 100.3 | 100.9 | 100.9 | 100.5 | −0.1 | % |

TABLE 7

Norepinephrine Bitartrate Inj. 16 μg/mL in 0.9% NaCl not sterilized with OXYGEN ABSORBER

| Product name | Norepinephrine Inj. 16 μg/mL in 0.9% NaCl |
|---|---|
| Batch Number | RD030-16 |
| Storage Conditions | 40° C. ± 2° C./RH 15% ± 5% - NOT Sterilized |

| TEST | LIMIT | T = 0 | T = 1M | T = 2M | T = 3M | T = 6M | UNIT |
|---|---|---|---|---|---|---|---|
| Appearance of Solution | Clear and colourless | Clear and colourless | Clear and colourless | Clear and colourless | Clear and colourless | Clear and colourless | / |
| pH | 3.0-4.5 | 3.6 | 3.7 | 3.7 | 3.7 | 3.7 | pH units |
| Osmolality | 270-320 | 290 | 295 | 290 | 290 | 290 | mOsmol/Kg |
| Assay | 90.0-115.0 | 100.6 | 100.3 | 100.9 | 100.9 | 100.5 | % |

TABLE 8

Norepinephrine Bitartrate Inj. 64 μg/mL in 0.9% NaCl not sterilized with OXYGEN ABSORBER

| Product name | Norepinephrine Inj. 64 μg/mL in 0.9% NaCl |
|---|---|
| Batch Number | RD031-16 |
| Storage Conditions | 40° C. ± 2° C./RH 15% ± 5% - NOT Sterilized |

| TEST | LIMIT | T = 0 | T = 1M | T = 2M | T = 3M | T = 3M | UNIT |
|---|---|---|---|---|---|---|---|
| Appearance of Solution | Clear and colorless | Clear and colorless | Clear and colorless | Clear and colorless | Clear and colorless | Clear and colorless | — |
| pH | 3.0-4.5 | 3.6 | 3.6 | 3.7 | 3.7 | 3.7 | pH units |
| Osmolality | 270-320 | 293 | 289 | 292 | 287 | 288 | mOsmol/Kg |
| Assay | 90.0-115.0 | 99.8 | 97.5 | 96.1 | 100.3 | 99.2 | % |

Obviously, numerous modifications and variations of the present invention are possible in light of the above teachings. It is therefore to be understood that within the scope of the appended claims, the invention may be practiced otherwise than as specifically described herein.

The invention claimed is:

1. A sterile, antioxidant-free aqueous norepinephrine solution packaged in a flexible plastic container in a sealed over-wrap pouch containing an oxygen absorber consisting essentially of between about 0.010 and 0.2 mg/ml of norepinephrine concentration as free base, a tonicity adjusting agent to provide an osmolality of from 260 and 320 mosm/kg, and sufficient acid and optionally a base to provide a pH of from about 3.6 to 3.8, with the remainder water, and wherein dissolved oxygen in the solution has not been removed before filling the flexible plastic container with the solution, and wherein, after storage for from 12 months to about 24 months at room temperature of about 25° C., the solution remains clear and colorless and/or the solution contains 90% or more of an initial amount of norepinephrine.

2. The sterile, antioxidant-free aqueous norepinephrine solution of claim 1 wherein the norepinephrine concentration is between 0.015 and 0.07 mg/ml.

3. The sterile, antioxidant-free aqueous norepinephrine solution of claim 2 wherein the norepinephrine concentration is selected from about 0.016, about 0.032 and about 0.064 mg/nil of norepinephrine.

4. The sterile, antioxidant-free aqueous norepinephrine solution of claim 3 wherein the norepinephrine concentration is about 0.016 mg/ml.

5. The sterile, antioxidant-free aqueous norepinephrine solution of claim 3 wherein the norepinephrine concentration is about 0.032 mg/ml.

6. The sterile, antioxidant-free aqueous norepinephrine solution of claim 3 wherein the norepinephrine concentration is about 0.064 mg/ml.

7. The sterile, antioxidant-free aqueous norepinephrine solution of claim 1 wherein the tonicity adjusting agent is sodium chloride.

8. The sterile, antioxidant-free aqueous norepinephrine solution of claim 7 wherein the amount of sodium chloride is between about 8 and 10 mg/ml.

9. The sterile, antioxidant-free aqueous norepinephrine solution of claim 8 wherein the amount of sodium chloride is between about 8.5 and 9.5 mg/ml.

10. The sterile, antioxidant-free aqueous norepinephrine solution of claim 9 wherein the amount of sodium chloride is about 9 mg/ml.

11. The sterile, antioxidant-free aqueous norepinephrine solution of claim 1 wherein the solution was aseptically sterilized.

12. The sterile, antioxidant-free aqueous norepinephrine solution of claim 1 wherein the flexible plastic container is packaged in a sealed over-wrap pouch containing an oxygen absorber and an oxygen indicator.

13. The sterile, antioxidant-free aqueous norepinephrine solution of claim 1 wherein the pH is greater than 3.6 and less than or equal to 3.8.

14. The sterile, antioxidant-free aqueous norepinephrine solution of claim 1 wherein the pH is 3.7 to 3.8.

15. The sterile, antioxidant-free aqueous norepinephrine solution of claim 1 wherein the flexible plastic container is filled with the solution aseptically.

* * * * *